US011446150B1

(12) United States Patent
Scott et al.

(10) Patent No.: US 11,446,150 B1
(45) Date of Patent: Sep. 20, 2022

(54) METHODS AND APPARATUSES FOR ATTACHMENT OF POROUS COATINGS TO IMPLANTS AND PRODUCTS THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Marcus L. Scott, Memphis, TN (US); Vivek D. Pawar, Germantown, TN (US); Carolyn L. Weaver, Collierville, TN (US); Daniel A. Heuer, Santa Rosa, CA (US); Roger R. Dees, Jr., Drummonds, TN (US); Forrest A. James, Oakland, TN (US); Matthew J. Quick, Memphis, TN (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 117 days.

(21) Appl. No.: 16/987,579

(22) Filed: Aug. 7, 2020

Related U.S. Application Data

(60) Provisional application No. 63/041,405, filed on Jun. 19, 2020, provisional application No. 62/984,015, filed on Mar. 2, 2020, provisional application No. 62/888,874, filed on Aug. 19, 2019.

(51) Int. Cl.
*A61F 2/30* (2006.01)
*A61F 2/38* (2006.01)

(52) U.S. Cl.
CPC .... *A61F 2/3094* (2013.01); *A61F 2002/3093* (2013.01); *A61F 2002/30784* (2013.01); *A61F 2002/30967* (2013.01); *A61F 2002/3863* (2013.01); *A61F 2310/00023* (2013.01);
(Continued)

(58) Field of Classification Search
CPC .............................................. A61F 2002/30967
See application file for complete search history.

(56) References Cited

U.S. PATENT DOCUMENTS

| 5,037,438 A | 8/1991 | Davidson |
| 5,104,410 A | 4/1992 | Chowdhary |
| 7,550,209 B2 | 6/2009 | Pawar et al. |

(Continued)

OTHER PUBLICATIONS

"Comparison of cross-sections of different femoral components for revision total knee replacement" by Carmen Zietz Philipp Bergschmidt, Andreas Fritsche, Daniel Kluess, Wolfram Mittelmeier, and Rainer Bader., Journal of Orthopaedic Surgery, 20(1):32-6, Apr. 2012.

*Primary Examiner* — Javier G Blanco
(74) *Attorney, Agent, or Firm* — KDB Firm PLLC (57) ABSTRACT

There are provided herein methods and products resulting therefrom. The methods include attaching a pre-fabricated porous ingrowth structure to a substrate by applying heat, or creating and bonding an in-situ-formed porous ingrowth structure from beads on a substrate by applying heat. In some embodiments, an oxidized metal surface of the substrate is diffusion hardened during the heating process. In some embodiments, a vacuum is applied during the heating process. In some embodiments, pressure is applied during the heating process. Also provided herein are assemblies for compressing the pre-fabricated porous ingrowth structure or the beads onto the substrate during the heating process.

13 Claims, 10 Drawing Sheets

(52) U.S. Cl.
CPC .............. *A61F 2310/00029* (2013.01); *A61F 2310/00089* (2013.01); *A61F 2310/00131* (2013.01)

(56) References Cited

U.S. PATENT DOCUMENTS

| | | |
|---|---|---|
| 8,128,703 B2 | 3/2012 | Hazebrouck et al. |
| 9,629,723 B2 | 4/2017 | Parisi et al. |
| 10,772,731 B2 | 9/2020 | Stalcup et al. |
| 2005/0184134 A1 | 8/2005 | Charlebois et al. |
| 2016/0250394 A1 | 9/2016 | Pawar et al. |

METHODS AND APPARATUSES FOR ATTACHMENT OF POROUS COATINGS TO IMPLANTS AND PRODUCTS THEREOF

CROSS REFERENCE TO RELATED APPLICATIONS

This application claims the benefit of U.S. Provisional Application No. 62/888,874, filed Aug. 19, 2019 and entitled "METHOD FOR ATTACHMENT OF A POROUS COATING", U.S. Provisional Application No. 62/984,015, filed Mar. 2, 2020 and entitled "METHOD FOR ATTACHMENT OF A POROUS COATING", and U.S. Provisional Application No. 63/041,405 filed Jun. 19, 2020 and entitled "METHODS AND APPARATUSES FOR ATTACHMENT OF POROUS COATINGS TO IMPLANTS AND PRODUCTS THEREOF". The disclosures of each of these applications is incorporated herein by reference.

FIELD OF THE DISCLOSURE

The present disclosure relates generally to orthopedic implants and methods and apparatuses for producing the same. In particular, the present disclosure relates orthopedic implants having porous surfaces and to methods and apparatuses for producing the same.

BACKGROUND

Certain medical implants and orthopedic implants require strength for weight bearing purposes and porosity to encourage bone/tissue in-growth. For example, many orthopedic implants include porous sections that provide a scaffold structure to encourage bone in-growth during healing and a weight bearing section intended to render the patient ambulatory. There is a continuing need in the art for improvements to such structures and to methods of making the same.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure is directed to methods and apparatuses for forming implants by bonding one or more porous metallic ingrowth structures to one more surfaces of a biocompatible alloy implant body and to implants made using such methods and apparatuses, including hip implants, knee implants, shoulder implants, ankle implants, spinal implants, trauma implants, mid-shaft implants, arthrodesis implants, UniSpacers, and cartilage replacements, among others.

As used herein, "biocompatible alloy" is defined as the alloy combinations that are currently used in orthopedic industry. Examples of such alloys include cobalt-chromium alloys such as cobalt-chromium-molybdenum alloys, titanium alloys such as titanium-aluminum-vanadium alloys, nickel-titanium alloys, zirconium alloys such as zirconium-niobium alloys, and further alloys that are made from zirconium, titanium, tantalum, niobium, hafnium or combinations any two, any three, any four, or all five of these metals, among others. In various embodiments, the biocompatible alloy implant body may comprise a zirconium alloy, among others. As used herein, "zirconium alloy" is defined broadly, and includes alloys having at least 5% (w/w) zirconium. The zirconium alloy can comprise zirconium and one or more of niobium, titanium or hafnium. The alloys can be polycrystalline or amorphous or single crystals or combinations of same.

In various embodiments, the one more surfaces of the biocompatible alloy implant body to which the one or more porous metallic ingrowth structures are bonded comprise one or more bone-interfacing alloy surfaces, including one or more non-articulating bone-interfacing alloy surfaces and/or one or more articulating bone-interfacing alloy surfaces, of the biocompatible alloy implant body.

In various embodiments, an interlayer of metallic powder or a collapsible metallic layer may be placed between the one or more porous metallic ingrowth structures and the one more bone-interfacing alloy surfaces of the biocompatible alloy implant body. In various embodiments, the metallic powder or the or collapsible metallic layer may be formed from a metal or metal alloy selected from titanium, titanium alloys, tantalum, tantalum alloys, cobalt-chromium alloys, zirconium, and zirconium alloys.

In various embodiments, the biocompatible alloy implant body may comprise one or more articulating implant body surfaces, which may correspond, for example, to one or more oxidized surfaces of the biocompatible alloy of the implant body.

In various embodiments, the one or more porous metallic ingrowth structures may be pre-fabricated porous metallic ingrowth structures.

In various embodiments, the one or more porous metallic ingrowth structures may be in-situ-created porous metallic ingrowth structures.

In various embodiments, the one or more porous metallic ingrowth structures may comprise a porous metallic pad and, optionally, a nonporous metallic base for the porous metallic pad.

In various embodiments, the one or more porous metallic ingrowth structures are formed from a metal or metal alloy selected from titanium, titanium alloys, tantalum, tantalum alloys, cobalt-chromium alloys, zirconium, and zirconium alloys.

In various aspects, the present disclosure pertains to methods of forming implants comprising a biocompatible alloy implant body and one or more bonded porous metallic ingrowth structures bonded to one more bone-interfacing alloy surfaces of the biocompatible alloy implant body, the method comprising: forming an assembly by (a) placing one or more preformed porous metallic ingrowth structures over the one more bone-interfacing alloy surfaces of the biocompatible alloy implant body or (b) placing metallic beads over the one more bone-interfacing alloy surfaces of the biocompatible alloy implant body; and heating the assembly to a temperature and for a time sufficient (a) to cause solid-state diffusion bonding of the one or more preformed porous metallic ingrowth structures to the one more bone-interfacing alloy surfaces of the biocompatible alloy implant body, thereby forming the one or more bonded porous metallic ingrowth structures or (b) to cause solid-state diffusion bonding of the metallic beads to one another and to the one more bone-interfacing alloy surfaces of the biocompatible alloy implant body, thereby forming the one or more bonded porous metallic ingrowth structures (i.e., in-situ-created porous metallic ingrowth structures).

In some embodiments, the methods further comprise placing an interlayer of metallic powder or a collapsible metallic layer between the one or more preformed porous metallic ingrowth structures and the one more bone-interfacing alloy surfaces of the biocompatible alloy implant body.

In some embodiments, the methods further comprise (a) applying a force to compress the one or more preformed porous metallic ingrowth structures onto the one more bone-interfacing alloy surfaces of the biocompatible alloy implant body during the heating of the assembly or (b) applying a force to compress the metallic beads together and to compress the metallic beads onto the one more bone-interfacing alloy surfaces of the biocompatible alloy implant body during the heating of the assembly.

Various additional aspects the present disclosure are directed to methods in which an assembly is formed by (a) bringing one or more preformed porous metallic ingrowth structures into contact with one more bone-interfacing alloy surfaces of a biocompatible alloy implant body or (b) placing metallic beads in contact with one more bone-interfacing alloy surfaces of a biocompatible alloy implant body.

In various embodiments, the assembly is then heated to a temperature and for a time sufficient (a) to cause solid-state diffusion bonding of the one or more preformed porous metallic ingrowth structures to the one more bone-interfacing alloy surfaces of the biocompatible alloy implant body or (b) to cause solid-state diffusion bonding of the metallic beads to one another (thereby forming one or more in-situ-created porous metallic ingrowth structures) and to the one more bone-interfacing alloy surfaces of the biocompatible alloy implant body.

Typical heating temperatures for the above methods may range from 600 to 1000 C, more typically 560 to 750 C, among other values. Typical bonding times for the above methods may range from 1 to 10 hours, among other values.

In various embodiments, the assembly is configured to apply a force to compress the one or more preformed porous metallic ingrowth structures or the metallic beads onto the one more bone-interfacing alloy surfaces of the biocompatible alloy implant body during the heat treatment process. For example, in some embodiments, the compressive stress may range from 0.5 to 40 MPa, among other values. One determinant of the compressive force is to avoid buckling of the porous structure at higher temperature. Thus, if a porous structure is designed to take more compressive stress, a higher compressive stress can be applied.

For this purpose, the assembly may comprise at least two fixture blocks and one or more compressing elements (e.g., bolts, nuts, screws or clamps, such as c-clamps) for drawing (e.g., by pulling or pushing) the fixture blocks together and compressing the one or more preformed porous metallic ingrowth structures or the metallic beads onto the one more bone-interfacing surfaces of the implant body. In some cases, one or more fixture blocks may be positioned over the preformed porous metallic ingrowth structures or the metallic beads on the one more bone-interfacing surfaces of the implant body, and one or more fixture blocks may be positioned over one or more articulating surfaces of the implant body. For instance, a single fixture may be provided over one or more bone-interfacing surfaces of the implant body, or multiple fixtures may be provided over multiple bone-interfacing surfaces of the implant body. Similarly, a single fixture may be provided over one or more articulating surfaces of the implant body, or multiple fixtures may be provided over multiple articulating surfaces of the implant body.

In some embodiments, the biocompatible alloy implant body further comprises one or more articulating surfaces which correspond to one or more oxidized surfaces of the biocompatible alloy of the implant body, in which case the assembly may be heated to a temperature and for a time sufficient to provide a diffusion hardened layer of increased thickness on the one or more articulating surfaces. Thus, there is provided a method to simultaneously produce an implant having 1) an oxide and a diffusion hardened layer on one or more articulating surfaces and 2) one or more mechanically integral porous metallic ingrowth structures on one or more bone-interfacing surfaces. Suitable heating temperatures and times are provided above.

In some embodiments, the assembly is heated under vacuum such that the one or more preformed porous metallic ingrowth structures or the one or more in-situ-created porous metallic ingrowth structures undergo minimal oxidation during the process.

As used herein, the term "vacuum" refers to a pressure of less than about $10^{-2}$ torr.

In certain embodiments, the assembly is heated under a vacuum that is less than $10^{-4}$ torr, less than $10^{-5}$ torr, or even less than $10^{-6}$ torr.

In some aspects, the present disclosure pertains to apparatuses for compressing one or more preformed porous metallic ingrowth structures or metallic beads onto one more bone-interfacing surfaces of an implant body, comprising (a) a plurality of fixture blocks and (b) one or more compressing elements for drawing the fixture blocks toward each other such that the one or more preformed porous metallic ingrowth structures or the metallic beads are compressed onto the one more bone-interfacing surfaces of the implant body. In some embodiments, one or more of the plurality of fixture blocks of the apparatuses may be configured to be positioned over the one or more preformed porous metallic ingrowth structures or the metallic beads on the one more bone-interfacing surfaces of the implant body, and one or more of the plurality of fixture blocks may be configured to be positioned over one or more articulating surfaces of the implant body.

As seen from the above, in some embodiments, the compressing elements are selected from bolts, nuts, screws or clamps. In some embodiments, the one or more compressing elements comprise a material selected from graphite, carbon fiber, stainless steel, or a ceramic material. In some embodiments, the plurality of fixture blocks comprise a material selected from graphite, tungsten, molybdenum, or a ceramic material.

In some aspects, the present disclosure pertains to assemblies that comprise: an implant body comprising one or more bone-interfacing alloy surfaces; one or more preformed porous metallic ingrowth structures disposed over the one more bone-interfacing alloy surfaces, or a plurality of metallic beads disposed over the one more bone-interfacing alloy surfaces; a plurality of fixture blocks; and one or more compressing elements, wherein the compressing elements draw at least two of the fixture blocks toward each other such that the one or more preformed porous metallic ingrowth structures or the metallic beads are compressed onto the one more bone-interfacing surfaces of the implant body.

In some embodiments, the biocompatible alloy implant body further comprises one or more articulating surfaces, which may, for example, correspond to one or more oxidized surfaces of the biocompatible alloy of the biocompatible alloy implant body, in which case at least one of the plurality of fixture blocks may be in contact with the one more bone-interfacing surfaces and at least one of the plurality of fixture blocks may be in contact with the one or more articulating surfaces.

Further features and advantages of at least some of the embodiments of the present disclosure, as well as the operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION OF EMBODIMENTS

The following description of the depicted embodiments is merely exemplary in nature and is in no way intended to limit the invention, its application, or uses.

In one embodiment, there is provided a method and a product resulting thereof, wherein the method includes attaching a pre-fabricated porous titanium (Ti) ingrowth structure or creating an in-situ porous ingrowth structure on a zirconium alloy during a diffusion hardening process of oxidized zirconium. As an example, the zirconium alloy may be Zr-2.5Nb. A porous Ti layer (e.g., Ti foam or beads) is placed in contact with the bone-interfacing portion (i.e., non-articulating or articulating bone-interfacing surfaces) of a base zirconium component. In some embodiments, an interlayer of titanium or zirconium powder is placed between the porous layer and the base component. The assembly is then subjected to a diffusion hardening process. The thermal cycle (time, temperature) associated with the diffusion hardening process is sufficient to cause solid-state diffusion bonding of the porous Ti layer to the substrate. If necessary, pressure may be applied to the assembly to improve the bonding between the porous Ti layer and the substrate. In some embodiments, the diffusion hardening process is done at high vacuum such that the Ti ingrowth structure undergoes minimal oxidation during the process, thereby retaining its original mechanical properties. The resulting product has a bone-ingrowth structure, an oxide, and a diffusion hardened zone on the articulating portion of the implant. Thus, there is provided a method to simultaneously produce on an oxidized zirconium component 1) an oxide and diffusion hardened zone on the articulating surfaces and 2) a mechanically and chemically integral porous Ti ingrowth structure on the bone-interfacing surfaces. Such product with a porous coating may be a hip, knee, shoulder, or spinal implant, among others.

Figure 1:
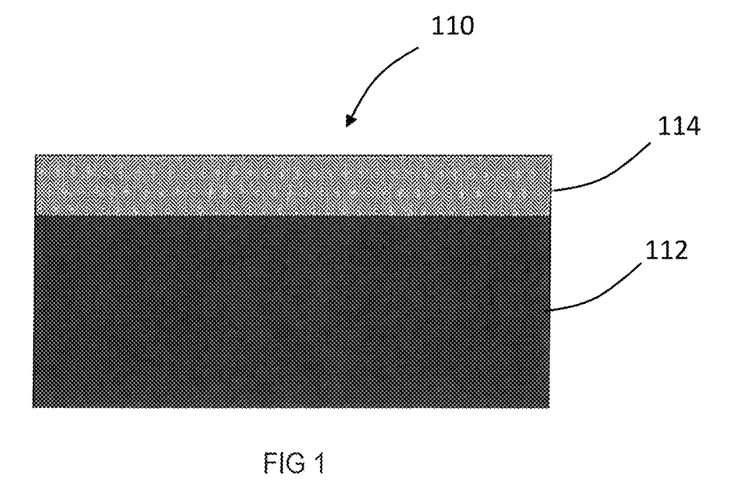
FIG. 1 illustrates an assembly of a substrate and a porous coating prior to diffusion hardening.
Figure 2:
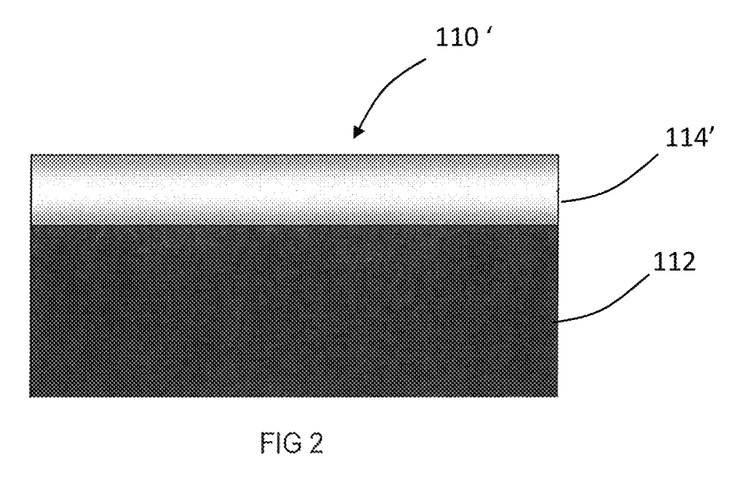
FIG. 2 illustrates an assembly of a substrate and a porous coating prior to diffusion hardening.

FIG. 1 illustrates an assembly 110 having a substrate 112 and a porous layer 114. As noted above, the substrate 112 may be zirconium alloy and the porous layer 114 may be titanium. The assembly 110 is then subjected to a diffusion hardening process. As seen in FIG. 2, the porous layer 114' is at least partially diffused in the substrate 112 of the assembly 110'.

Figure 3:
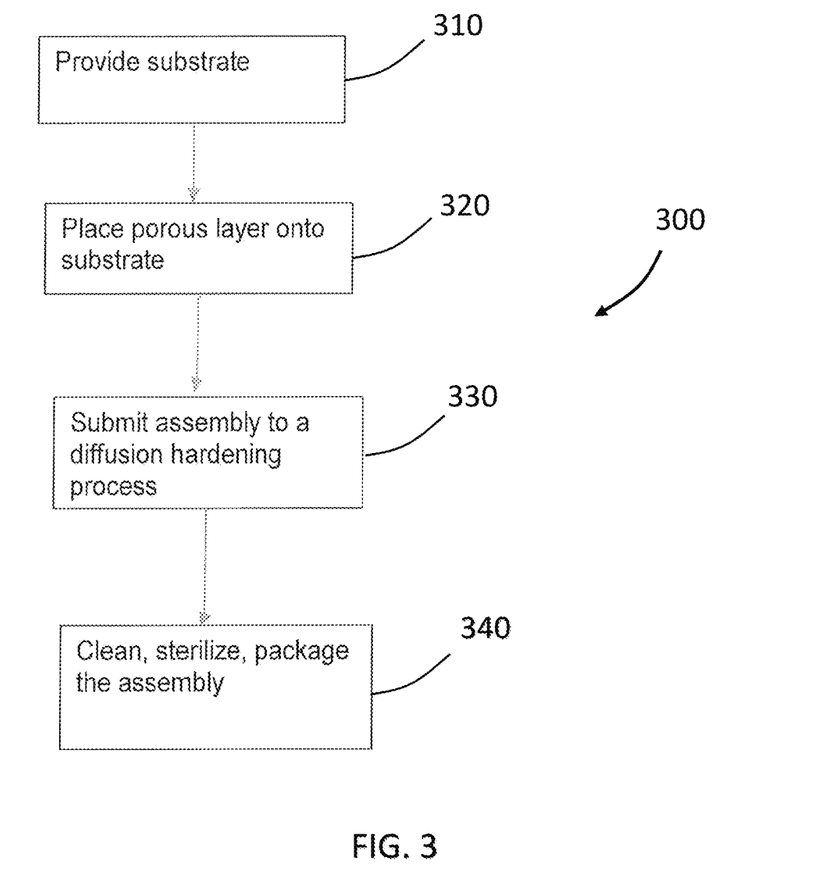
FIG. 3 illustrates a flowchart of a method for attaching a porous coating.

Referring now to FIG. 3, the method 300 includes a step 310 of providing a substrate. In step 320, the porous layer is placed onto the substrate. The assembly is then subjected to a diffusion hardening process in step 330. The thermal cycle (time, temperature) associated with the diffusion hardening process is sufficient to cause solid-state diffusion bonding of the porous Ti layer to the substrate. In an optional step, a mechanical force or pressure may be applied to the assembly to improve the bonding between the porous layer and the substrate. Chemical or physical treatments may be performed beforehand to allow for uniform contact between the bonding surfaces. Examples of physical treatments include blasting or grinding. Examples of chemical treatments include acidic or alkaline treatments to remove asperities on the bonding surfaces, In some embodiments, the diffusion hardening process is done at high vacuum such that the Ti ingrowth structure undergoes minimal oxidation during the process, thereby retaining its original mechanical properties. The resulting product has a bone-ingrowth structure, an oxide, and a diffusion hardened zone on the articulating portion of the implant. Thereafter, in step 340, the assembly may be cleaned, sterilized, and packaged.

Figure 4A:
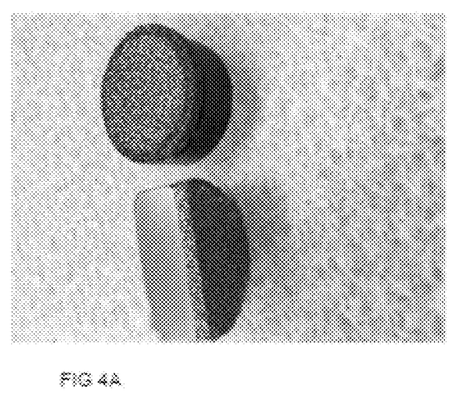
FIG. 4A illustrates samples of an assembly of a substrate and a porous coating.
Figure 4B:
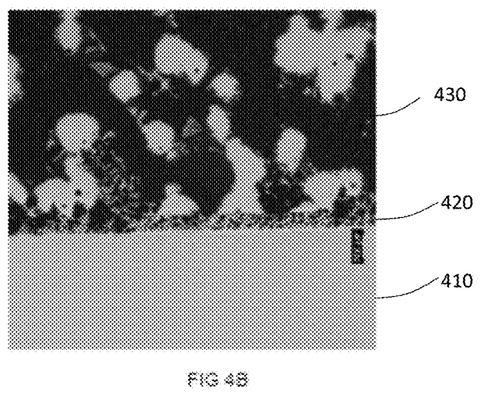
FIG. 4B illustrates microstructure of an assembly of a substrate and a porous coating in a first example.

In a first example, a 3-D printed porous titanium pad is diffusion bonded to oxidized Zr-2.5Nb substrate. In some embodiments, an interlayer of fine titanium or zirconium powder is placed between the porous layer and the base component. Temperature is maintained at 800 C for a duration of four hours and a vacuum less than $10^{-4}$ Torr. FIG. 4A illustrates the sintered samples, with the sample at the bottom being sectioned. FIG. 4B illustrates a cross-sectional image showing bonding of the porous pad 430 with the intermediate titanium powder layer 420 bonded to the substrate 410.

Figure 5:
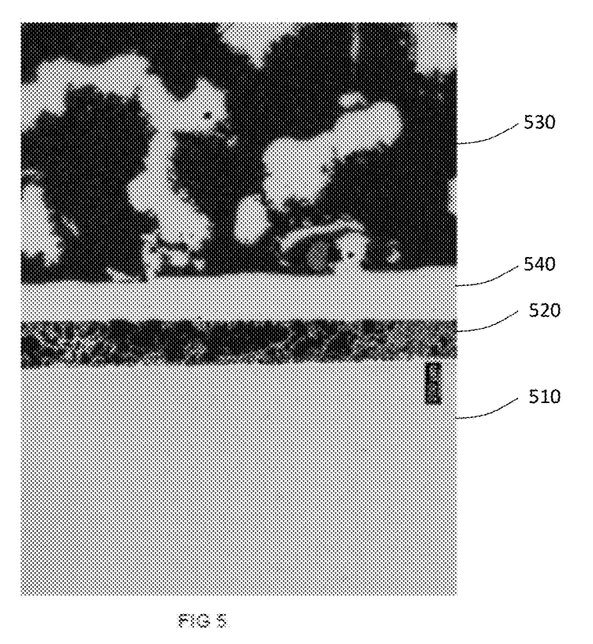
FIG. 5 illustrates microstructure of assembly of a substrate and a porous coating in a second example.

In a second example, a 3-D printed porous titanium pad with a solid base is diffusion boded to oxidized Zr-2.5Nb substrate. In some embodiments, an interlayer of fine titanium or zirconium powder is placed between the porous layer and the base component. Temperature is maintained at 800 C for a duration of four hours and a vacuum less than $10^{-4}$ Torr. FIG. 5 illustrates a cross-sectional image showing bonding of the porous pad 530 with the solid base 540 to the substrate 510 using the intermediate layer of titanium powder 520.

Figure 19:
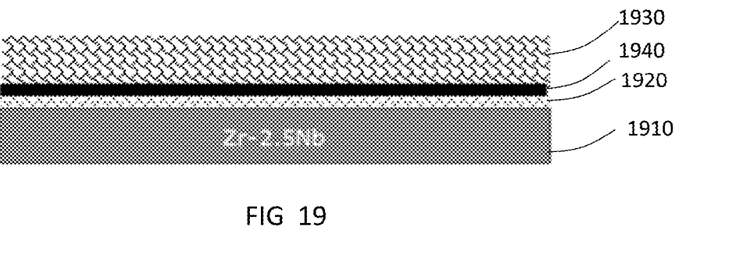
FIG. 19 illustrates a cross-sectional image showing bonding of porous pad with a solid base to a substrate using an intermediate collapsible metallic layer.

In some embodiments, a thin collapsible metallic layer (e.g., a collapsible titanium or zirconium layer) is placed between the porous pad and the substrate. FIG. 19 illustrates a cross-sectional image showing bonding of a porous pad 1930 having a solid base 1940 to a substrate 1910 using an intermediate collapsible metallic layer 1920. Such a collapsible metallic layer may be manufactured, for example, by additive manufacturing (AM) or by 3D printing, which will create a larger surface for bonding. The structure is configured to collapse/crumble under compression thereby creating an interface.

In one embodiment, there is a method comprising: providing a solid oxidized zirconium component, the articulating surfaces are composed of a ceramic zirconium oxide outer surface and the bone-interfacing surfaces is composed of Zr-2.5Nb alloy; providing an open-celled, reticulated Ti foam ingrowth structure or Ti beads; placing the ingrowth structure against the bone-interfacing zirconium alloy surfaces of the implant, thereby forming an assembly; subjecting the assembly to the thermal profile and controlled atmosphere associated with a diffusion hardening process in order to simultaneously increase the thickness of the diffusion hardened layer on the articulating surfaces and to metallurgically bond the ingrowth structure to the zirconium alloy substrate on the bone-interfacing surfaces.

In a second embodiment, there is a method comprising: providing a solid oxidized zirconium component, the articulating surfaces of which is composed of a ceramic zirconium oxide outer surface and the bone-interfacing surfaces of which is composed of Zr-2.5Nb alloy; providing an open-celled, reticulated Ti foam ingrowth structure; placing the ingrowth structure against the bone-interfacing zirconium alloy surfaces of the implant, thereby forming an assembly; subjecting the assembly to the thermal profile and controlled atmosphere associated with a diffusion hardening process, during which pressure is applied to the assembly, in order to simultaneously increase the thickness of the diffusion hardened layer on the articulating surfaces and to metallurgically bond the ingrowth structure to the zirconium alloy substrate on the bone-interfacing surfaces.

As an example of the second embodiment, seven (7) Zr-2.5Nb disks were oxidized using an electric furnace for 1 hour and 50 minutes at 635 C. One side of each disk was ground to a smooth surface finish (approximately 2400 grit) for attachment. Seven (7) pads, each having a thickness of 1 mm, were built with a 250 µm solid titanium alloy layer at the base and a 750 µm titanium porous structure. The solid base layer of each pad was also ground to a smooth surface finish (approximately 2400 grit) for attachment. Each pad was attached to each Zr-2.5Nb substrate to create an assembly. The smooth surfaces of each disk and pad were placed flush to each other and a compressive force was applied to the assembly. The measured force applied was approximately 1,500 lbf. For a 1 in. coupon, this is approximately 13.2 MPa (1.9 ksi). Each assembly with the applied force was then placed into the vacuum furnace. The assemblies were heated to 750 C for 2 hours and then vacuum cooled back to room temperature. The assemblies were then removed from the furnace and the applied force was removed. The mean and standard deviation of the tensile attachment strength of all seven assemblies was 49.9±9.3 MPa (7.2±1.3 ksi).

In a third embodiment, there is a method comprising: providing a solid oxidized zirconium component, the articulating surfaces of which is composed of a ceramic zirconium oxide outer surface and the bone-interfacing surfaces of which is composed of Zr-2.5Nb alloy; providing spherical Ti beads; providing a binding mixture composed of binding agents and Ti powder; applying the binding mixture to the Ti beads and zirconium alloy substrate; placing the Ti beads against the bone-interfacing zirconium alloy surfaces of the implant, thereby forming an assembly; subjecting the assembly to the thermal profile and controlled atmosphere associated with a diffusion hardening process, during which pressure is applied to the assembly, in order to simultaneously increase the thickness of the diffusion hardened layer on the articulating surfaces and to metallurgically bond adjacent Ti beads to one another and to bond the Ti beads to the zirconium alloy substrate on the bone-interfacing surfaces.

In a fourth embodiment, there is a method comprising: providing a solid oxidized zirconium component, the articulating surfaces of which is composed of a ceramic zirconium oxide outer surface and the bone-interfacing surfaces of which is composed of Zr-2.5Nb alloy; providing a mixture composed of Ti powder, with or without binding agents and a pore former, such as urea; placing the mixture against the bone-interfacing zirconium alloy surfaces of the implant, thereby forming an assembly; subjecting the assembly to the thermal profile and controlled atmosphere associated with a diffusion hardening process in order to simultaneously increase the thickness of the diffusion hardened layer on the articulating surfaces and to create a porous titanium ingrowth layer and metallurgically bond this layer to the zirconium alloy substrate on the bone-interfacing surfaces.

In a fifth embodiment, there is a method comprising: providing a solid oxidized zirconium component, the articulating surfaces of which is composed of a ceramic zirconium oxide outer surface and the bone-interfacing surfaces of which is composed of Zr-2.5Nb alloy; providing a mixture composed of Ti powder, with or without binding agents and a pore former such as urea; placing the mixture against the bone-interfacing zirconium alloy surfaces of the implant, thereby forming an assembly; subjecting the assembly to the thermal profile and controlled atmosphere associated with a diffusion hardening process, during which pressure is applied to the assembly, in order to simultaneously increase the thickness of the diffusion hardened layer on the articulating surfaces and to create a porous titanium ingrowth layer and metallurgically bond this layer to the zirconium alloy substrate on the bone-interfacing surfaces.

Alternatives to the Ti foam structure described in the first and second embodiments could include any mechanically integral Ti porous layer, such as a pad of pre-sintered Ti beads or pre-sintered fiber metal mesh.

Alternatives to the spherical Ti beads described in the third embodiment could be Ti particles of any shape, such as irregular, asymmetric Ti powder.

In one aspect of the disclosure the porous in growth structure can be further coated with hydroxyapatite coating. The hydroxyapatite coating can be applied using plasma spray process or can be deposited from a solution.

Other metals, such as tantalum and tantalum alloys, cobalt-chromium alloys, zirconium and zirconium alloys and titanium alloys, could comprise the ingrowth structure listed in all the embodiments of the disclosure.

In further aspects of the present disclosure, an assembly is provided which is configured to apply a force to compress one or more preformed porous metallic ingrowth structures or metallic beads onto one more bone-interfacing alloy surfaces of a biocompatible alloy implant body during the head treatment process.

For this purpose, the assembly may further comprise at least two fixture blocks and one or more compressing elements (e.g., bolts, clamps, etc.) for pulling or pushing the fixture blocks together and compressing the one or more preformed porous metallic ingrowth structures or the metallic beads onto the one more bone-interfacing surfaces of the implant body. For example, one or more fixture blocks may be positioned over the preformed porous metallic ingrowth structures or the metallic beads on the one more bone-interfacing surfaces of the implant body. For instance, a single fixture may be provided over one or more bone-interfacing surfaces of the implant body, or multiple fixtures may be provided over multiple bone-interfacing surfaces of the implant body. Similarly, one or more fixture blocks may be positioned over one or more articulating surfaces of the implant body. For instance, a single fixture may be provided over one or more articulating surfaces of the implant body, or multiple fixtures may be provided over multiple articulating surfaces of the implant body. Exemplary materials for the fixture blocks include graphite, tungsten, molybdenum, and ceramic materials such as alumina or yttria stabilized zirconia, aluminum nitrides, boron carbides, tungsten carbides, silicon carbides, silicon nitride, and silicates. Materials for the compressing elements include graphite, carbon fiber, stainless steel and ceramic materials such as alumina or yttria stabilized zirconia. The fixtures can be coated with inert materials. For example, graphite fixtures may be coated with yttria stabilized zirconia or alumina or hydroxyapatite to minimize surface contamination.

Two exemplary assemblies will now be described with reference to FIGS. 6-18, which illustrate two embodiments wherein a plurality of porous metallic pads are bonded to bone-interfacing alloy surfaces of a femoral implant body. For example, titanium porous pads can be bonded to a zirconium alloy femoral implant body, where good results have been found to come from diffusion bonding which employs both heat and pressure.

Figure 9:
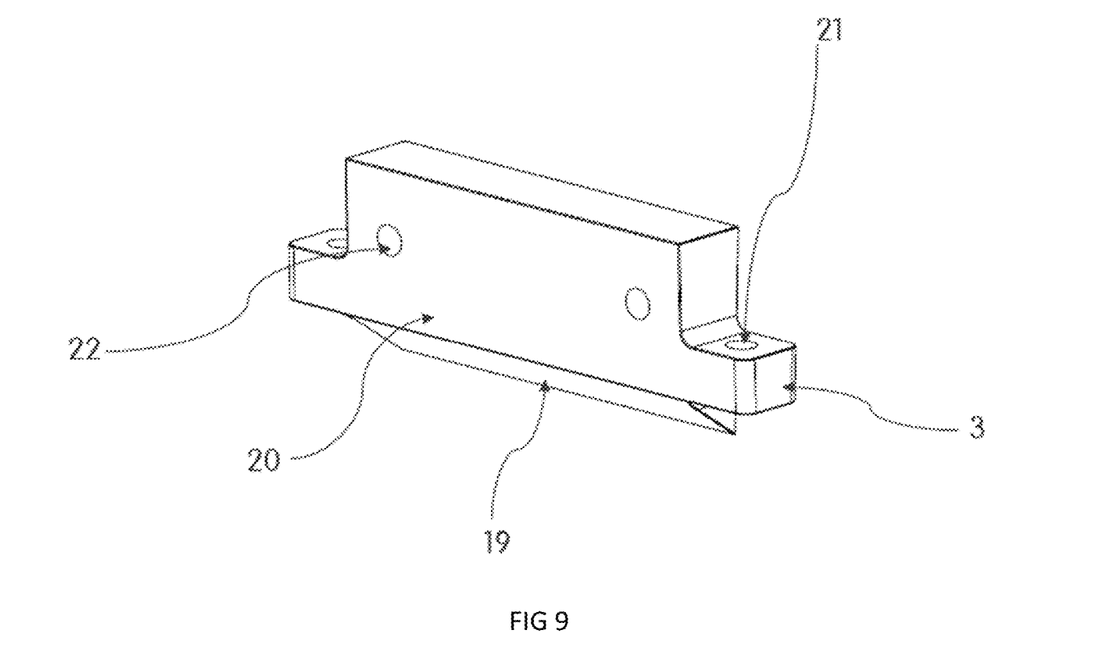
FIG. 9 illustrates a fixture block (3), in accordance with an embodiment of the present disclosure.
Figure 10:
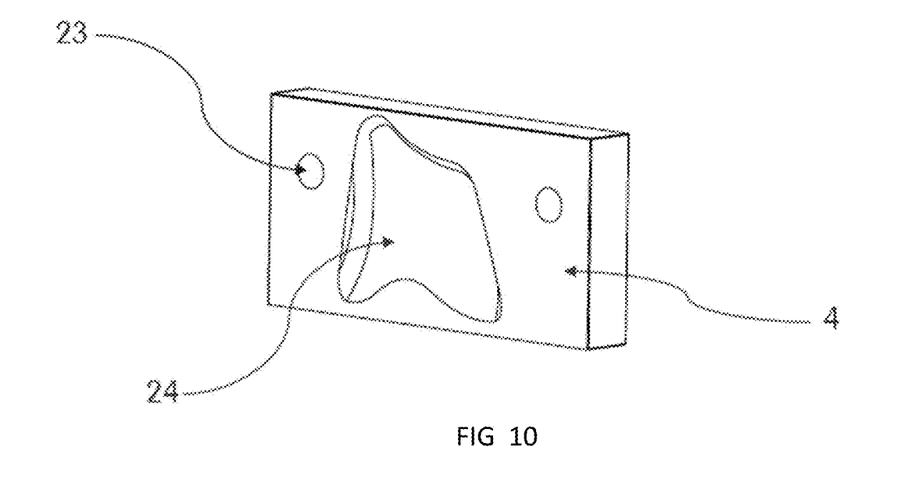
FIG. 10 illustrates a fixture block (4), in accordance with an embodiment of the present disclosure.
Figure 11:
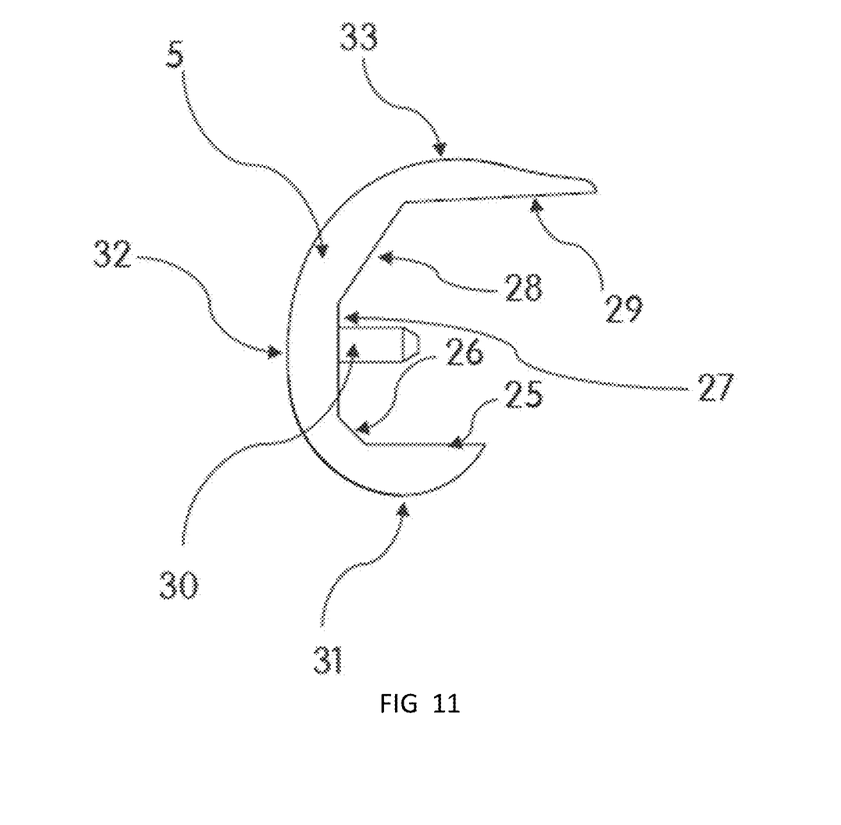
FIG. 11 illustrates a femoral implant from a mediolateral view, in accordance with an embodiment of the present disclosure.

Turning now to FIGS. 6-12, an assembly is described wherein whereby a plurality of porous pads compressed are onto bone-interfacing alloy surfaces of a femoral implant body (5), which is shown in FIG. 11 and includes a posterior flat surface (25), a posterior chamfer surface (26), a distal flat surface (27), an anterior chamfer surface (28), an anterior flat surface (29), two pegs (30) (one shown), a posterior articular surface (31), a distal articular surface (32), and an anterior articular surface (33).

Figure 6:
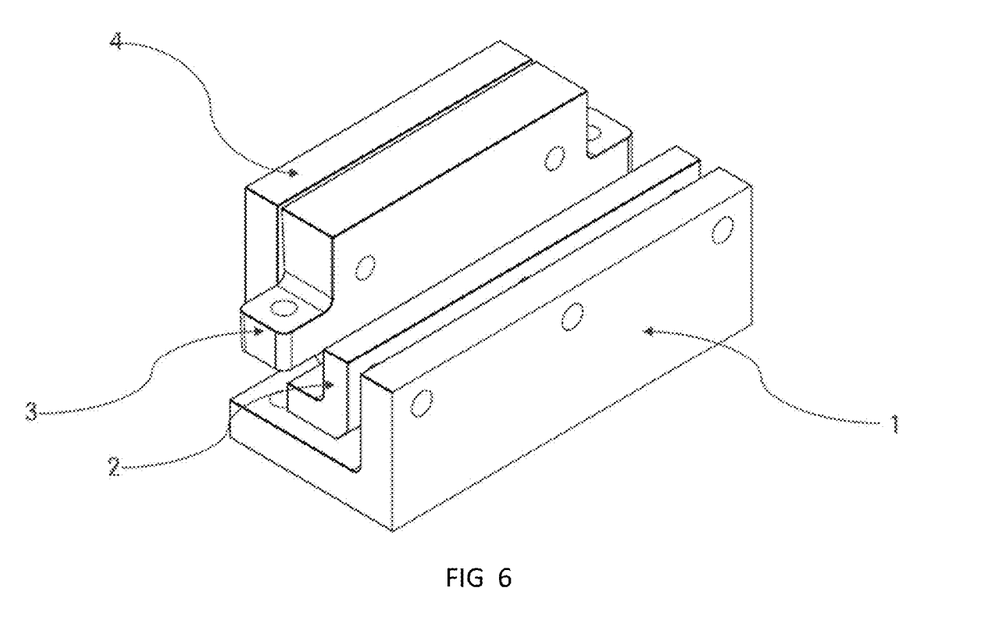
FIG. 6 illustrates relative positions of fixture blocks of an assembly for a heat treatment process, in accordance with an embodiment of the present disclosure.

FIG. 6 illustrates relative positions of fixture blocks (1), (2), (3), (4) of an assembly during the treatment process whereby a plurality of porous pads are compressed onto bone-interfacing alloy surfaces (25), (26), (27), (28), (29) of the femoral implant body (5).

Figure 12:
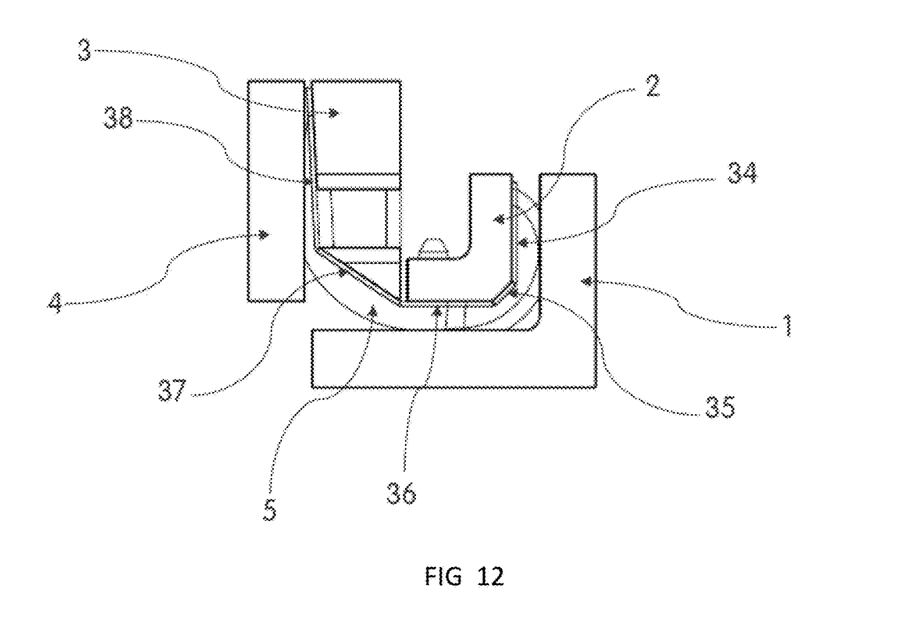
FIG. 12 illustrates an assembly during a heat treatment process, in accordance with an embodiment of the present disclosure.

FIG. 12 illustrates an assembly of the fixture blocks (1), (2), (3), (4) the femoral implant body (5), and porous pads (34), (35), (36), (37), (38) which are compressed onto bone-interfacing alloy surfaces (25), (26), (27), (28), (29) of the femoral implant body (5).

Figure 7:
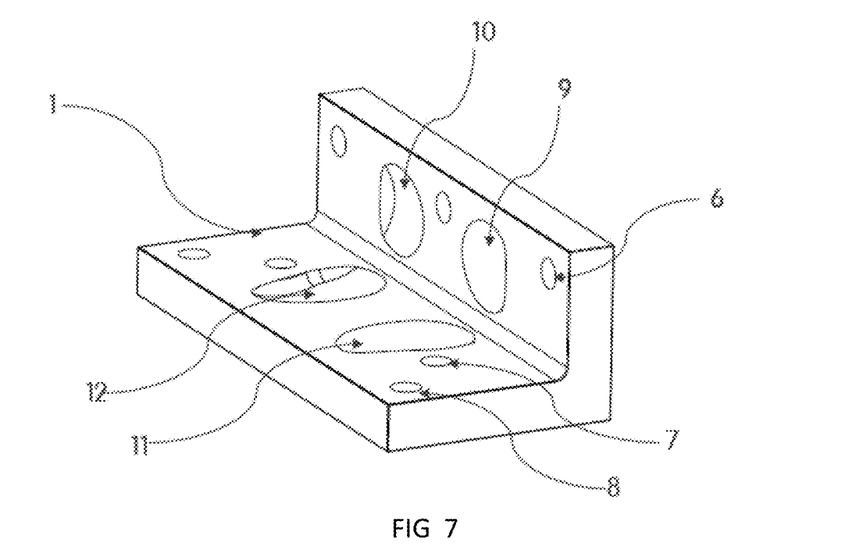
FIG. 7 illustrates a fixture block (1), in accordance with an embodiment of the present disclosure.

Fixture block (1) is shown in FIG. 7 and includes the following features: one hole (6) of three posterior holes illustrated that allow for fixture block (1) to mate with fixture block (2) through nut and bolt connections, this applies pressure to the posterior flat surface (25) and posterior chamfer surface (26) with porous pads (34), (35) during the heat treatment process; one hole (7) of two distal holes illustrated that allow for fixture block (1) to mate with fixture block (2) through nut and bolt connections, which applies pressure to the distal flat surface (27), and the posterior chamfer surface (26) of the femoral implant body (5) with porous pads (35), (36) during the heat treatment process; and one hole (8) of two distal holes illustrated that allow for fixture block (1) to mate with fixture block (3) through nut and bolt connections, which applies pressure to the anterior chamfer surface (28) with porous pad (37) during the heat treatment process. Fixture block (1) of FIG. 7 also shows a groove (9) similar to the lateral posterior condyle articular surface of the femoral implant body (5), a groove (10) similar to the medial posterior condyle articular surface of the femoral implant body (5), a groove (11) similar to the lateral distal articular surface of the femoral implant body, and a groove (12) similar to the medial distal articular surface of the femoral implant body, allowing the femoral implant body (5) to seat in the correct position and orientation during the heat treatment process.

Figure 8:
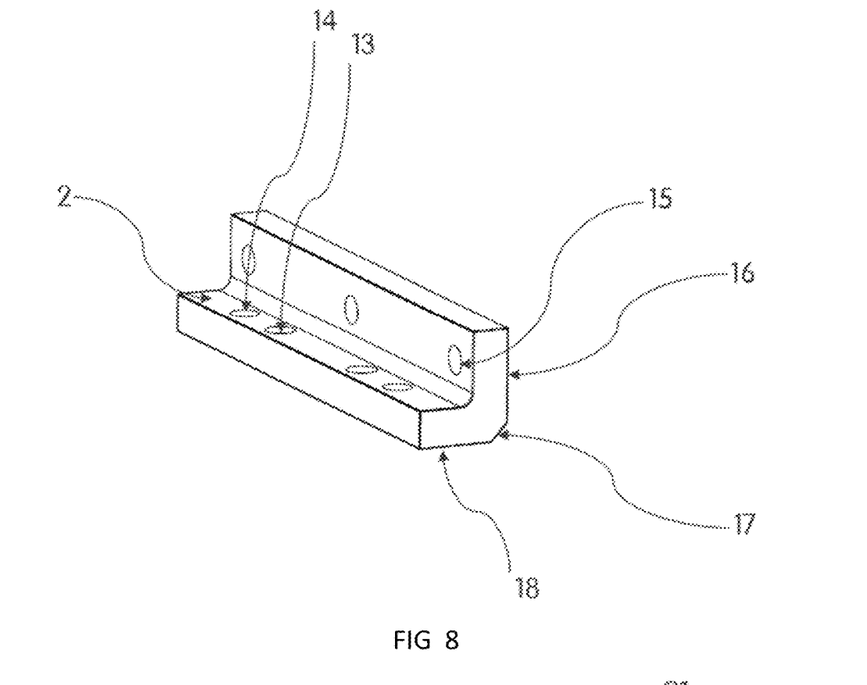
FIG. 8 illustrates a fixture block (2), in accordance with an embodiment of the present disclosure.

Fixture block (2) is shown in FIG. 8 and includes the following features: one hole (13) of two distal holes illustrated that allow for the femoral pegs of the femoral implant body (5) pass through the fixture block (2); one hole (14) of two distal holes illustrated to allow for fixture block (2) to mate with fixture block (1) through nut and bolt connections, which applies pressure to the distal flat surface (27) of the femoral implant body (5); and one hole (15) of three posterior holes illustrated to allow for fixture block (2) to mate with fixture block (1) through nut and bolt connections, which applies pressure to the posterior flat surface (25) and posterior chamfer surface (26) with the porous pads (34), (35) during the heat treatment process. Fixture block (2) shown in FIG. 8 also includes a flat surface (16) which mates to the posterior flat surface (25) of the femoral implant body to apply pressure to the porous pad (34) against the femoral implant body during the heat treatment process, a flat surface (17) which mates to the posterior chamfer surface (26) of the femoral implant body to apply pressure to the porous pad (35) against the femoral implant body during the heat treatment process, and a flat surface (18) which mates to the distal surface (27) of the femoral implant body to apply pressure to the porous pad (36) against the femoral implant body during the heat treatment process.

Fixture block (3) is shown in FIG. 9 and includes the following features: a flat surface (19) which mates to the anterior chamfer surface (28) of the femoral implant body (5) to apply pressure to the porous pad (37) against the femoral implant body (5) during the heat treatment process; and a flat surface (20), which mates to the anterior flat surface (29) of the femoral implant body (5) to apply pressure to the porous pad (38) against the femoral implant body (5) during the heat treatment process. Fixture block (3) shown in FIG. 9 further shows: one hole (21) of two distal holes illustrated to allow for fixture block (3) to mate with fixture block (1) through nut and bolt connections, which applies pressure to the anterior chamfer surface (28) with the porous pad (37) during the heat treatment process; and one hole (22) of two anterior holes illustrated to allow for fixture block (3) to mate with fixture block (4) through nut and bolt connections, which applies pressure to the anterior flat surface (29) of the femoral implant body (5) with the porous pad (38) during the heat treatment process.

Fixture block (4) is shown in FIG. 10 and shows: one hole (23) of two anterior holes illustrated to allow for fixture block (4) to mate with fixture block (3) through nut and bolt connections, which applies pressure to the anterior flat surface (29) of the femoral implant body (5) with the porous pad (38) during the heat treatment process; and a groove (24) similar to the anterior articular surface (33) of the femoral implant body (5), allowing the femoral implant body (5) to seat in the correct position and orientation during the heat treatment process.

Figure 17:
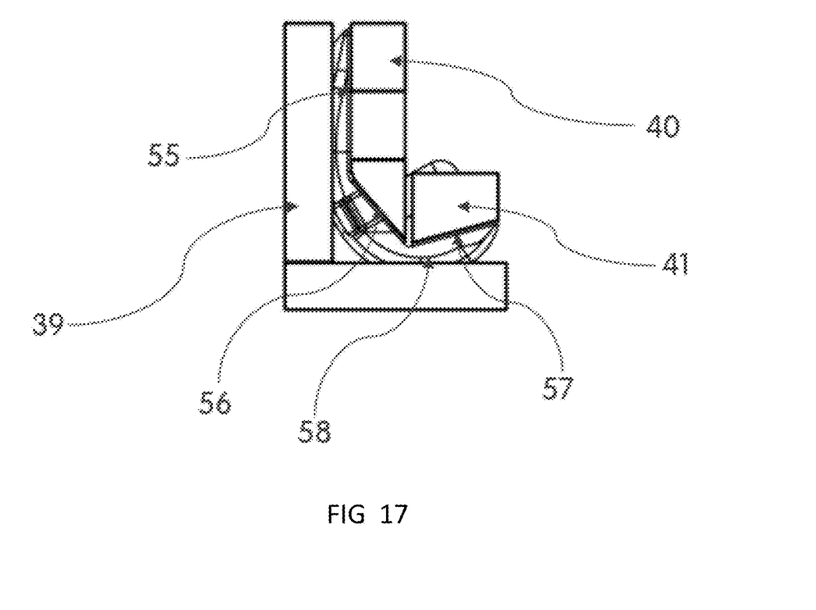
FIG. 17 illustrates an assembly during heat treatment process, in accordance with an embodiment of the present disclosure.
Figure 18:
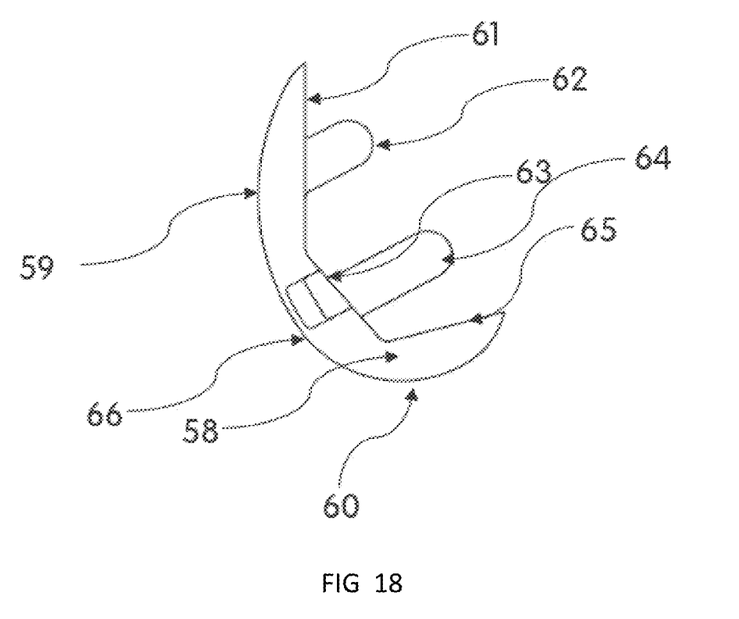
FIG. 18 illustrates a femoral implant from a mediolateral view, in accordance with an embodiment of the present disclosure.

Another exemplary assembly will now be described with reference to FIGS. 13-18 whereby a plurality of porous pads are compressed onto bone-interfacing alloy surfaces of a unicompartmental femoral implant body (58), which is shown in FIG. 18 and includes an anterior articular surface (59), a posterior articular surface (60), an anterior flat surface (61), an anterior flat surface peg (62), an anterior chamfer surface (63), an anterior chamfer surface peg (64), a posterior flat surface (65), and a distal articular surface (66).

Figure 13:
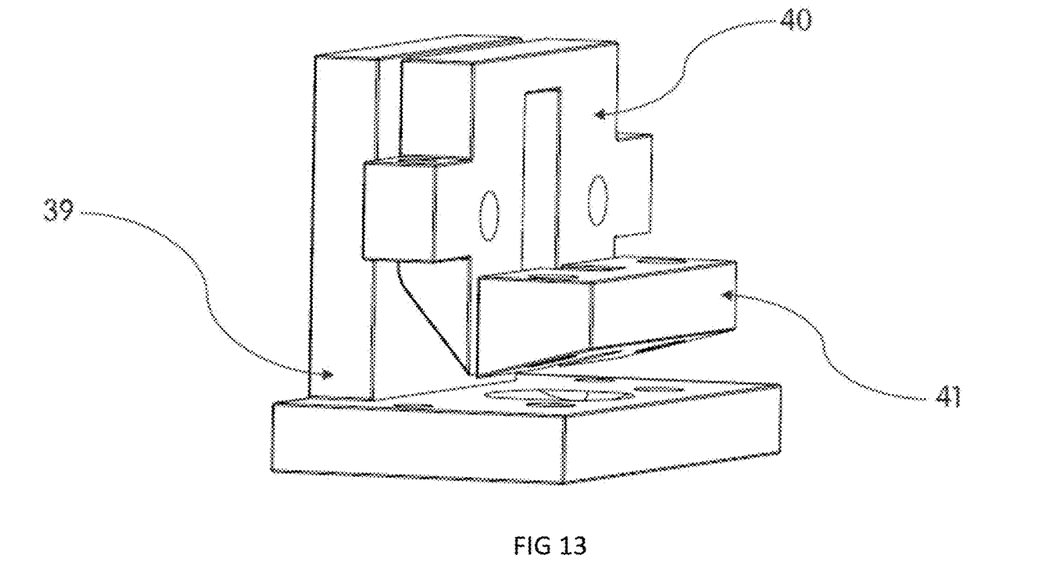
FIG. 13 illustrates a relative positions of fixture blocks of an assembly for a heat treatment process, in accordance with an embodiment of the present disclosure.

FIG. 13 illustrates relative positions of fixture blocks (39), (40), (41) of an assembly during a heat treatment process whereby a plurality of porous pads are compressed onto bone-interfacing alloy surfaces (61), (63), (65) of the unicompartmental femoral implant body (58).

FIG. 17 illustrates an assembly of the fixture blocks (39), (40), (41), the unicompartmental femoral implant body (58), and porous pads (55), (56), (57) which are compressed onto bone-interfacing alloy surfaces (61), (63), (65) of the unicompartmental femoral implant body (58). Specifically, porous pad (55) is positioned on the anterior flat surface (61) of the unicompartmental femoral implant body (58), porous pad (56) is positioned on the anterior chamfer surface (63) of the unicompartmental femoral implant body (58), and porous pad (57) is positioned on the posterior flat surface (65) of the unicompartmental femoral implant body (58).

Figure 14:
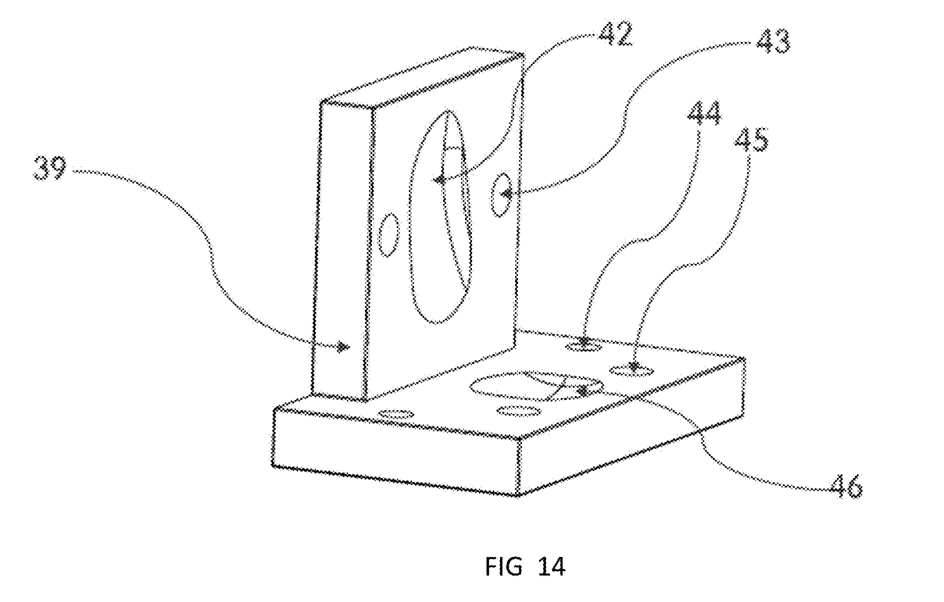
FIG. 14 illustrates a fixture block (39), in accordance with an embodiment of the present disclosure.

Fixture block (39) is shown in FIG. 14, which is configured to mate with the anterior articular surface (59) and the posterior articular surface (60) of the unicompartmental femoral implant body (58) and includes the following features: a groove (42) similar to that of the anterior articular surface (59) of the unicompartmental femoral implant body (58), allowing the unicompartmental femoral implant body (58) to seat in the correct position and orientation; one hole (43) of two anterior holes illustrated that allow for fixture block (39) to mate with fixture block (40) through nut and bolt connections, which applies pressure to the anterior flat surface (61) of the unicompartmental femoral implant body (58) and the porous pad (55) during the heat treatment process; one hole (44) of two distal holes illustrated that allow for fixture block (39) to mate with fixture block (40) through nut and bolt connections, which applies pressure to the anterior chamfer surface (63) of the unicompartmental femoral implant body (58) and the porous pad (56) during the heat treatment process; one hole (45) of two distal holes illustrated that allow for fixture block (39) to mate with fixture block (41) through nut and bolt connections, which applies pressure to the posterior flat surface (65) of the unicompartmental femoral implant body (58) and the porous pad (57) during the heat treatment process, and a groove (46) similar to that of the posterior articular surface (60) of the unicompartmental femoral implant body (58), which allows the unicompartmental femoral implant body (58) to seat in the correct position and orientation.

Figure 15:
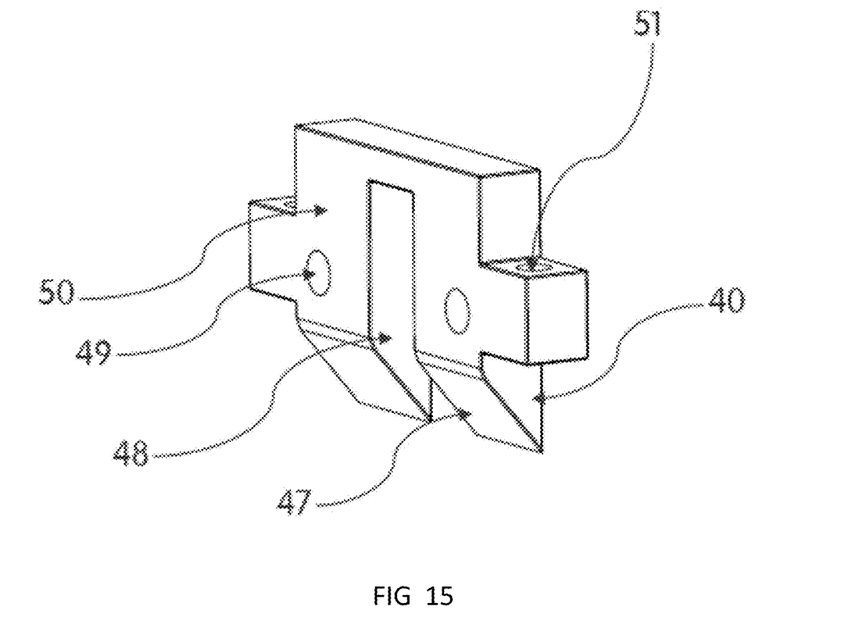
FIG. 15 illustrates a fixture block (40), in accordance with an embodiment of the present disclosure.

Fixture block (40) is shown in FIG. 15, which is configured to mate with the anterior flat surface (61) and anterior chamfer surface (63) of the unicompartmental femoral implant body (58) and includes the following features: a flat surface (47) which mates to the anterior chamfer surface (63) of the unicompartmental femoral implant body (58) to apply pressure to the porous pad (56) against the unicompartmental femoral implant body (58) during the heat treatment process; a gap (48) in fixture block (40) to allow for the pegs (62), (64) of the unicompartmental femoral implant body (58) to pass through, in order to allow correct alignment and orientation throughout the heat treatment process; one hole (49) of two anterior holes illustrated that allow for fixture block (40) to mate with fixture block (39) through nut and bolt connections, this applies pressure to the anterior flat surface (61) of the unicompartmental femoral implant body (58) and the porous pad (55) during the heat treatment process; a flat surface (50) which mates to the anterior flat surface (61) of the unicompartmental femoral implant body (58) to apply pressure to the porous pad (55) against the unicompartmental femoral implant body (58) during the heat treatment process; and one hole (51) of two distal holes illustrated that allow for fixture block (40) to mate with fixture block (39) through nut and bolt connections, which applies pressure to the anterior chamfer (63) of the unicompartmental femoral implant body (58) and the porous pad (56) during the heat treatment process.

Figure 16:
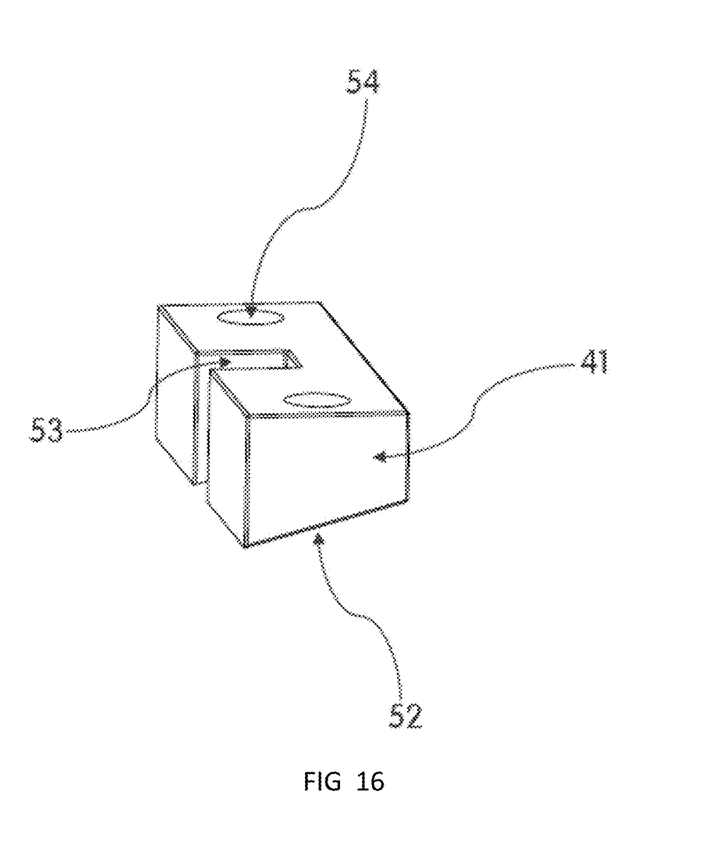
FIG. 16 illustrates a fixture block (41), in accordance with an embodiment of the present disclosure.

Fixture block (41) is shown in FIG. 16, which is configured to mate with the posterior flat surface (65) of the unicompartmental femoral implant body (58) and includes the following features: a flat surface (52) which mates to the posterior flat surface (65) of the unicompartmental femoral implant body (58) to apply pressure to the porous pad (57) against the femoral implant body during the heat treatment process; a gap (53) in fixture block (41) to allow for the pegs (64) of the unicompartmental femoral implant body (58) to pass through, in order to allow correct alignment and orientation throughout the heat treatment process; and one hole (54) of two distal holes illustrated that allow for fixture block (41) to mate with fixture block (39) through nut and bolt connections, which applies pressure to the posterior flat surface (65) of the unicompartmental femoral implant body (58) and the porous pad (57) during the heat treatment process.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein.

What is claimed is:

1. A method of forming an implant comprising a biocompatible alloy implant body and one or more bonded porous metallic ingrowth structures bonded to one more bone-interfacing alloy surfaces of the biocompatible alloy implant body, the method comprising:
    forming an assembly including one more bone-interfacing alloy surfaces of the biocompatible alloy implant body;
    placing a collapsible metallic layer onto the one more bone-interfacing alloy surfaces of the biocompatible alloy implant body, wherein the collapsible metallic layer is configured to collapse/crumble under compression thereby creating an interface; and
    placing one or more preformed porous metallic ingrowth structures into contact with the collapsible metallic layer so that the collapsible metallic layer is between the one or more preformed porous metallic ingrowth structures and the one more bone-interfacing alloy surfaces of the biocompatible alloy implant body;
    heating the assembly to a temperature and for a time sufficient to cause solid-state diffusion bonding of the one or more preformed porous metallic ingrowth structures to the one more bone-interfacing alloy surfaces of the biocompatible alloy implant body, thereby forming the one or more bonded porous metallic ingrowth structures; and
    applying a force to compress the one or more preformed porous metallic ingrowth structures onto the one more bone-interfacing alloy surfaces of the biocompatible alloy implant body during the heating of the assembly, wherein the biocompatible alloy implant body further comprises one or more articulating implant body surfaces, and wherein the heating of the assembly creates a diffusion hardened layer of increased thickness on the one or more articulating surfaces.

2. The method of claim 1, wherein the temperature ranges from 500° C. to 1000° C.

3. The method of claim 1, wherein the time ranges from 1 to 10 hours.

4. The method of claim 1, wherein the biocompatible alloy of the implant body comprises an alloy selected from cobalt-chromium alloys, titanium alloys and zirconium alloys.

5. The method of claim 1, wherein the one or preformed porous metallic ingrowth structures are formed from a metal or metal alloy selected from titanium, titanium alloys, tantalum, tantalum alloys, cobalt-chromium alloys, zirconium, and zirconium alloys.

6. The method of claim 1, wherein the one or more articulating implant body surfaces correspond to one or more oxidized surfaces of the biocompatible alloy of the biocompatible alloy implant body.

7. The method of claim 1, wherein the one or more preformed porous metallic ingrowth structures comprises a porous metallic pad.

8. The method of claim 1, wherein the collapsible metallic layer is formed from a metal or metal alloy selected from titanium, titanium alloys, tantalum, tantalum alloys, cobalt-chromium alloys, zirconium, and zirconium alloys.

9. The method of claim 1,
    further comprising:
    providing an apparatus for compressing the one or more preformed porous metallic ingrowth structures onto one more bone-interfacing surfaces of an implant body, the apparatus comprising (a) a plurality of fixture blocks and (b) one or more compressing elements for drawing the fixture blocks toward each other such that the one or more preformed porous metallic ingrowth structures are compressed onto the one more bone-interfacing surfaces of the implant body.

10. The method of claim 9, wherein one or more of the plurality of fixture blocks are configured to be positioned over the one or more preformed porous metallic ingrowth structures on the one more bone-interfacing surfaces of the implant body, and one or more of the plurality of fixture blocks are configured to be positioned over one or more articulating surfaces of the implant body.

11. The method of claim 9, wherein the compressing elements are selected from bolts, nuts, screws or clamps.

12. The method of claim 9, wherein the plurality of fixture blocks comprise a material selected from graphite, tungsten, molybdenum, or a ceramic material.

13. The method of claim 9, wherein the one or more compressing elements comprise a material selected from graphite, carbon fiber, stainless steel, or a ceramic material.

* * * * *